(12) United States Patent
Weeber et al.

(10) Patent No.: US 8,292,953 B2
(45) Date of Patent: Oct. 23, 2012

(54) MULTIFOCAL INTRAOCULAR LENS

(75) Inventors: Hendrik A Weeber, Groningen (NL);
Patricia Ann Piers, Groningen (NL);
Mark H. Bandhauer, Orange, CA (US);
Marrie H. Van Der Mooren, Engelbert (NL); Huawei Zhao, Irvine, CA (US)

(73) Assignee: AMO Groningen B.V., Santa Ana, CA (US)

( * ) Notice: Subject to any disclaimer, the term of this patent is extended or adjusted under 35 U.S.C. 154(b) by 521 days.

(21) Appl. No.: 12/254,710

(22) Filed: Oct. 20, 2008

(65) Prior Publication Data
US 2010/0097569 A1    Apr. 22, 2010

(51) Int. Cl.
*A61F 2/16*    (2006.01)
(52) U.S. Cl. ......... 623/6.3; 623/6.28; 351/169; 351/171
(58) Field of Classification Search ................. 623/6.28, 623/6.3; 351/169, 171
See application file for complete search history.

(56) References Cited

U.S. PATENT DOCUMENTS

| | | | |
|---|---|---|---|
| 4,881,805 A | 11/1989 | Cohen | |
| 5,096,285 A | 3/1992 | Silberman | |
| 5,112,351 A * | 5/1992 | Christie et al. | 623/6.28 |
| 5,117,306 A * | 5/1992 | Cohen | 359/565 |
| 5,121,979 A | 6/1992 | Cohen | |
| 5,121,980 A | 6/1992 | Cohen | |
| 5,129,718 A | 7/1992 | Futhey et al. | |
| 5,144,483 A | 9/1992 | Cohen | |
| 5,225,858 A | 7/1993 | Portney | |
| 5,229,797 A | 7/1993 | Futhey et al. | |
| 5,589,982 A | 12/1996 | Faklis et al. | |
| 5,682,223 A * | 10/1997 | Menezes et al. | 623/6.28 |
| 5,684,560 A * | 11/1997 | Roffman et al. | 351/160 R |
| 5,715,031 A * | 2/1998 | Roffman et al. | 351/161 |
| 5,748,282 A | 5/1998 | Freeman | |
| RE36,150 E | 3/1999 | Gupta | |
| 6,325,510 B1 | 12/2001 | Golub et al. | |
| 6,536,899 B1 | 3/2003 | Fiala | |
| 6,557,998 B2 | 5/2003 | Portney | |
| 6,576,011 B2 | 6/2003 | Portney | |
| 6,609,793 B2 | 8/2003 | Norrby et al. | |
| 6,814,439 B2 | 11/2004 | Portney | |

(Continued)

FOREIGN PATENT DOCUMENTS

RU    2186417    7/2002

OTHER PUBLICATIONS

Cohen, "Diffractive Bifocal Lens Design", Optom. Vis. Sci 70(6) 461-468, (Jun. 1993).

(Continued)

*Primary Examiner* — Paul Prebilic
(74) *Attorney, Agent, or Firm* — AMO Groningen B.V.

(57) ABSTRACT

An intraocular lens for providing a subject with vision at various distances includes an optic having a first surface with a first shape, an opposing second surface with a second shape, a multifocal refractive profile, and one or more diffractive portions. The optic may include at least one multifocal diffractive profile. In some embodiments, multifocal diffractive and the multifocal refractive profiles are disposed on different, distinct, or non-overlapping portions or apertures of the optic. Alternatively, portions of the multifocal diffractive profiles and the multifocal refractive profiles may overlap within a common aperture or zone of the optic.

38 Claims, 4 Drawing Sheets

U.S. PATENT DOCUMENTS

| | | | |
|---|---|---|---|
| 6,830,332 | B2 | 12/2004 | Piers et al. |
| 6,951,391 | B2 | 10/2005 | Morris et al. |
| 7,025,456 | B2 | 4/2006 | Morris et al. |
| 7,073,906 | B1 | 7/2006 | Portney |
| 7,093,938 | B2 * | 8/2006 | Morris et al. ............ 351/168 |
| 7,188,949 | B2 | 3/2007 | Bandhauer et al. |
| 7,381,221 | B2 | 6/2008 | Lang et al. |
| 7,441,894 | B2 * | 10/2008 | Zhang et al. ............ 351/168 |
| 2002/0143394 | A1 * | 10/2002 | Lang ............ 623/6.28 |
| 2003/0045931 | A1 * | 3/2003 | Lang ............ 623/5.11 |
| 2003/0098162 | A1 * | 5/2003 | Cook ............ 166/380 |
| 2004/0156014 | A1 | 8/2004 | Piers et al. |
| 2006/0098162 | A1 | 5/2006 | Bandhauer et al. |
| 2006/0098163 | A1 * | 5/2006 | Bandhauer et al. ............ 351/161 |
| 2006/0116764 | A1 | 6/2006 | Simpson |
| 2006/0238702 | A1 * | 10/2006 | Glick et al. ............ 351/160 R |
| 2007/0032866 | A1 | 2/2007 | Portney |

OTHER PUBLICATIONS

Zhao et al. "The Effect of Chromatic Dispersion on Pseudo Phakic Optical Performance", J Opthalmol. 2007, 91:1225-1229, (May 2007).

Apple et al. "Intraocular Lenses: Evolution Design Complications and Pathology", (1989) William & Wilkins, (May 1989).

U.S. Appl. No. 12/254,677, filed Oct. 20, 2008.

U.S. Appl. No. 12/254,723, filed Oct. 20, 2008.

* cited by examiner

MULTIFOCAL INTRAOCULAR LENS

FIELD OF THE INVENTION

The present application generally relates to lenses and related methods that can replace or supplement the lens of a human eye, more particularly to multifocal lenses and related methods that provide two or more optical powers within a single optic or optical zone.

BACKGROUND OF THE INVENTION

Intraocular lenses (IOLs) and other ophthalmic lenses have been configured to provide multiple foci, for example, to provide both distant vision and near vision to a subject, thus at least approximating the accommodative ability of the natural lens in a younger subject. Examples of such lenses are disclosed in U.S. Pat. No. 6,536,899 to Fiala; U.S. Pat. Nos. 5,225,858; 6,557,998; 6,814,439; 7,073,906 to Portney; U.S. Pat. No. 7,188,949 to Bandhauer; and U.S. Pat. No. 7,093,938 to Morris, all of which are herein incorporated by reference in their entirety.

Such multifocal or bifocal ophthalmic lenses may generally be classified as multifocal diffractive lenses or multifocal refractive lenses. Various advantages and disadvantages have been associated with each class or type of multifocal lens. One approach for incorporating the benefits of each class of multifocal lens is to use a multifocal diffractive lens in one eye and a multifocal refractive lens in the other eye.

A common problem with multifocal IOLs is that of halo patterns or images that can occur when an out-of-focus image associated with one of the foci is superimposed with an in-focus image associated with another focus of the lens. For example, a distant automobile headlight, when seen through a typical diffractive bifocal lens, appears as an in-focus spot on the retina of the eye and an out-of-focus blur spot surrounding the in-focus spot and having a distinct outer border. This distinct outer border has been found to be annoying to users and various efforts have been made to soften this border so that the halo spot is less noticeable.

Multifocal ophthalmic lenses are needed that incorporate the advantages of both multifocal diffractive and multifocal refractive intraocular lenses within a single optic in synergistic ways that enhance the optical performance over traditional multifocal lenses and/or reduce the effects of halo images.

DETAILED DESCRIPTION OF THE DRAWINGS

Figure 1:
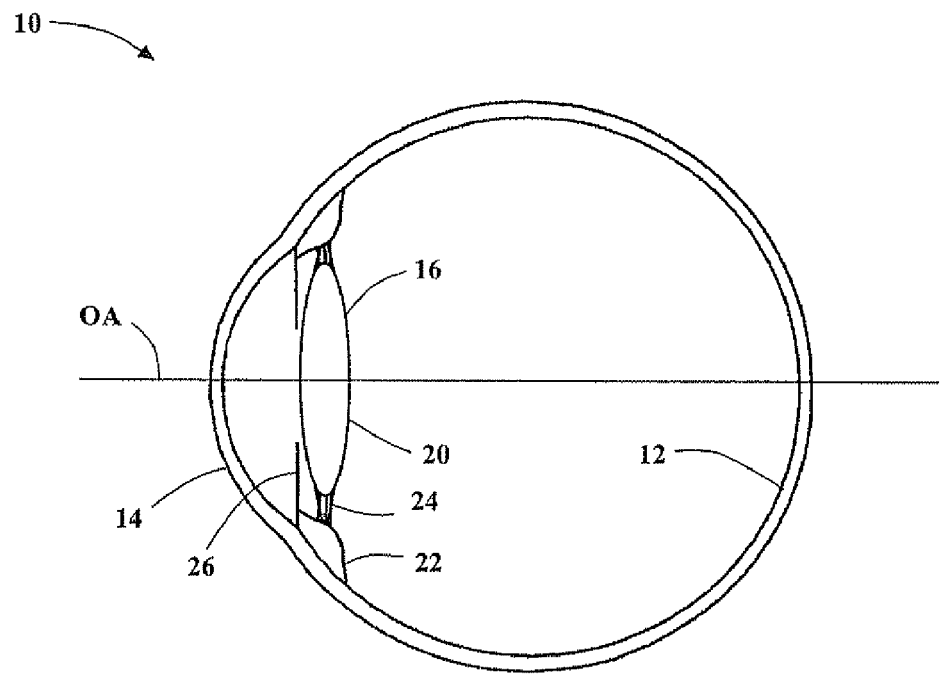
FIG. 1 is a side view of an eye containing a natural crystalline lens.

The present invention is directed to multifocal lenses, lens systems, and associated methods of making or use thereof. Embodiments discussed herein are generally directed to intraocular lenses; however, other types of lenses are anticipated, especially other types of ophthalmic lenses, such as contact lenses, corneal implants, spectacles, and the like. In some embodiments, a corneal surgical procedure, such as a LASIK or PRK procedure, are conducted to provide optical aspects of the lenses discussed below.

In certain embodiments, an optic provides multifocal and/or extended focus performance through the use of a multifocal refractive element or profile in combination with a diffractive element or profile. The diffractive element may be a bifocal or multifocal diffractive element, wherein light within the visible range of the electromagnetic spectrum is directed two or more diffraction orders and/or foci. Alternatively, the diffractive element may be a monofocal diffractive element, wherein light within the visible range of the electromagnetic spectrum is directed completely or substantially completely to a single diffraction order and/or focus. In certain embodiments, a multifocal diffractive profile is provided on all or part of one surface of an optic, while a multifocal refractive profile is provided on all or part of an opposite surface of the optic. Alternatively, the multifocal diffractive profile and the multifocal refractive profile may be provided on a common surface. In some embodiments, multifocal diffractive and the multifocal refractive profiles are disposed on different, distinct, or non-overlapping portions or apertures of the optic. Alternatively, portions of the multifocal diffractive profiles and the multifocal refractive profiles may overlap within a common aperture or zone of the optic. In any of these embodiments, combinations of a multifocal refractive element with a diffractive element may be configured to offer a design or designer more flexibility in providing a predetermined balance between near and distant vision as a function of pupil size or lighting conditions. Such combinations also be configured to soften halo images by providing more flexibility and design parameters for adjusting the distribution of light within a halo cross-section.

As used herein, the terms "about" or "approximately", when used in reference to a Diopter value of an optical power, mean within plus or minus 0.5 Diopter of the referenced optical power(s). As used herein, the terms "about" or "approximately", when used in reference to a percentage (%), mean within plus or minus one percent (±1%). As used herein, the terms "about" or "approximately", when used in reference to a linear dimension (e.g., length, width, thickness, distance, etc.) mean within plus or minus one percent (1%) of the value of the referenced linear dimension.

As used herein, the terms "light" or "visible light" mean electromagnetic radiation within the visible waveband, for example, electromagnetic radiation with a wavelength in a vacuum that is between 390 nanometers and 780 nanometers. As used herein, the term "optical power" of a lens or optic means the ability of the lens or optic to converge or diverge light to provide a focus (real or virtual) when disposed within a media having a refractive index of 1.336 (generally considered to be the refractive index of the aqueous and vitreous humors of the human eye), and is specified in reciprocal meters or Diopters (D). See ISO 11979-2. As used herein the terms "focus" or "focal length" of a lens or optic is the reciprocal of the optical power. As used herein the term "power" of a lens or optic means optical power. As used herein, the term "refractive power" or "refractive optical power" means the power of a lens or optic, or portion thereof, attributable to refraction of incident light. As used herein, the term "diffractive power" or "diffractive optical power" means the power of a lens or optic, or portion thereof, attributable to the diffraction or constructive interference of incident light into one or more diffraction orders. Except where noted otherwise, optical power (either absolute or add power) of an intraocular lens or associated optic is from a reference plane associated with the lens or optic (e.g., a principal plane of an optic). In this respect, an intraocular lens with a base or add power of 4.0 Diopters is approximately equal to an optical power of about 3.2 Diopters in a spectacle lens.

As used herein, the term "clear aperture" means the opening of a lens or optic that restricts the extent of a bundle of light rays from a distant source that can be imaged or focused by the lens or optic. The clear aperture is typically circular and specified by its diameter, although other shapes are acceptable, for example, oval, square, or rectangular. Thus, the clear aperture represents the full extent of the lens or optic usable for forming a conjugate image of an object or for focusing light from a distant point source to a single focus, or to a plurality of predetermined foci in the case of a multifocal optic or lens. It will be appreciated that the term clear aperture does not limit the transmittance of the lens or optic to be at or near 100%, but also includes lenses or optics having a lower transmittance at particular wavelengths or bands of wavelengths at or near the visible range of the electromagnetic radiation spectrum. In some embodiments, the clear aperture has the same or substantially the same diameter as the optic. Alternatively, the diameter of the clear aperture may be smaller than the diameter of the optic, for example, due to the presence of a glare or posterior capsular opacification (PCO) reducing structure disposed about a peripheral region of the optic.

As used herein, the term "diffraction efficiency" is defined as the light energy, power, or intensity at a particular wavelength that is diffracted into a particular diffraction order of a diffractive optic, element, or portion divided by the total light energy, power, or intensity at the particular wavelength that is useful in providing vision or that is contained in all diffractive orders configured to provide near, intermediate, or distant vision when placed in a model eye (real or mathematical) or in an eye of a patient or mammalian subject. By this definition, a monofocal diffractive optic, element, or portion has a diffraction efficiency of 100%, while a multifocal diffractive optic, element, or portion with blazed profile configured to produce zeroth and first diffraction orders in the visible range has a diffraction efficiency of 50% for each of two foci in the visible.

A multifocal optic, lens, refractive profile or structure, or diffractive profile or structure is generally characterized by base power and at least one add power. As used herein the term "base power", when used in reference to an optic or lens, means a power (in Diopters) of an optic or lens required to provide distant vision at the retina of a subject eye. As used herein the term "base power", when specifically applied to a refractive profile or diffractive profile, means a reference power (e.g., zero or about zero Diopters, or the power of a lower diffraction order of the diffractive profile used to provide more distant vision) from which one or more add powers of the profile or structure may be measured or compared. As used herein, the term "add power" means a difference in optical power (in Diopters) between a base power and a second power of an optic, lens, profile, or structure. When the add power is positive, the sum of the add power and the base power corresponds to a total optical power suitable for imaging an object at some finite distance from an eye onto the retina. A typical maximum add power for an optic or lens is the range of about 3 Diopter to about 4 Diopters in the plane of the lens; however, this number may be as high as 6 Diopters or more. An add power in Diopters may be directly related to an object distance from an eye by the relationship $d=1/D$, where d is the object distance in meters and D is the add power in Diopters. For example, an add power of 1 Diopter is suitable for focusing an object onto the retina that is located at a distance of 1 meter from an emmetropic eye in a disaccommodative state (e.g., with a relaxed ciliary muscle), while add powers of 0.5 Diopter, 2 Diopters, 3 Diopters, and 4 Diopters are suitable for focusing an object onto the retina that is located at a distance of 2 meters, 50 cm, 33 cm, and 25 cm, respectively, from an emmetropic eye in a disaccommodative state.

As used herein, the term "near vision" means vision produced by an eye that allows a subject to focus on objects that are at a distance of 40 cm or closer to a subject (i.e., at least 2.5 Diopters of add power), typically within a range of 25 cm to 33 cm from the subject (i.e., 3 Diopters to 4 Diopters of add power), which corresponds to a distance at which a subject would generally place printed material for the purpose of reading. As used herein, the term "intermediate vision" means vision produced by an eye that allows a subject to focus on objects that are located between 40 cm and 2 meters from the subject (i.e., having an add power between 2.5 Diopters and 0.5 Diopters). As used herein, the term "distant vision" means vision produced by an eye that allows a subject to focus on objects that are at a distance that is greater than 2 meters, typically at a distance of about 5 meters from the subject, or at a distance of about 6 meters from the subject, or greater.

Referring to FIG. 1, a cross-sectional view of a phakic eye containing the natural crystalline lens is shown in which an eye 10 includes a retina 12 that receives light in the form of an image produced when light from an object is focused by the combination of the optical powers of a cornea 14 and a natural crystalline lens 16. The cornea 14 and lens 16 are generally disposed about an optical axis OA. As a general convention, an anterior side is considered to be a side closer to the cornea 14, while a posterior side is considered to be a side closer to the retina 12.

The natural lens 16 is enclosed within a capsular bag 20, which is a thin membrane attached to a ciliary muscle 22 via zonules 24. An iris 26, disposed between the cornea 14 and the natural lens 16, provides a variable pupil that dilates under lower lighting conditions (mesopic or scotopic vision) and constricts under brighter lighting conditions (photopic vision). The ciliary muscle 24, via the zonules 24, controls the shape and position of the natural lens 16, allowing the eye 10 to focus on both distant and near objects. It is generally understood that distant vision is provided when the ciliary muscle 22 is relaxed, wherein the zonules 24 pull the natural lens 16 so that the capsular bag 20 and lens 16 are generally flatter and provide a longer focal length (lower optical power). It is generally understood that near vision is provided when the ciliary muscle contracts, thereby relaxing the zonules 24 and allowing the capsular bag 20 and lens 16 to return to a more rounded state that produces a shorter focal length (higher optical power).

Figure 2:
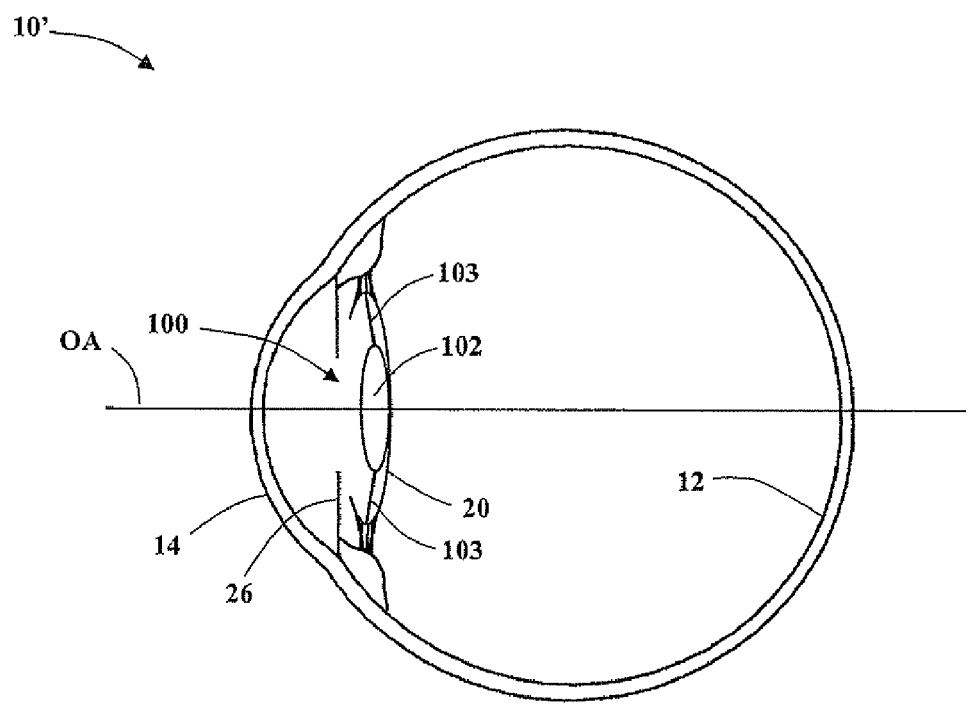
FIG. 2 is a side view of the eye in FIG. 1 with an intraocular lens according to an embodiment of the present invention.

Referring to FIG. 2, a cross-sectional view of a pseudophakic eye is shown in which the natural crystalline lens 16 has been replaced by an intraocular lens 100 according to an embodiment of the present invention. The intraocular lens 100 comprises an optic 102 and haptics 103, the haptics 103 being configured to at least generally center the optic 102 within the capsular bag 20, provide transfer of ocular forces to the optic 102, and the like. Numerous configurations of haptics 103 relative to optic 102 are well know within the art, and embodiments of the present invention may generally be applied to any of these. The optic 102 is configured to provide two or more foci, for example, to provide a subject with both distant vision and near vision, to provide a subject with both distant vision and intermediate vision, or provide a subject with distant vision, intermediate vision, and near vision, as is explained in greater detail below.

Figure 3:
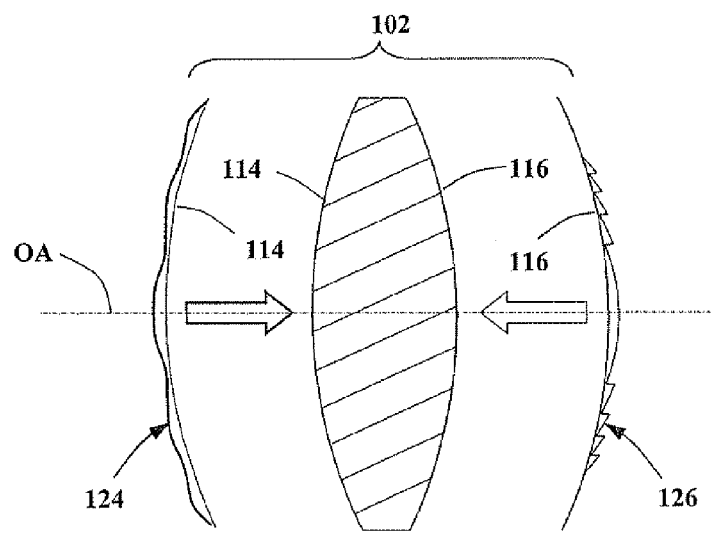
FIG. 3 is a side view of a cross-section of the intraocular lens shown in FIG. 2 showing diffractive and refractive profiles and their associated base shapes or curvatures.
Figure 4:
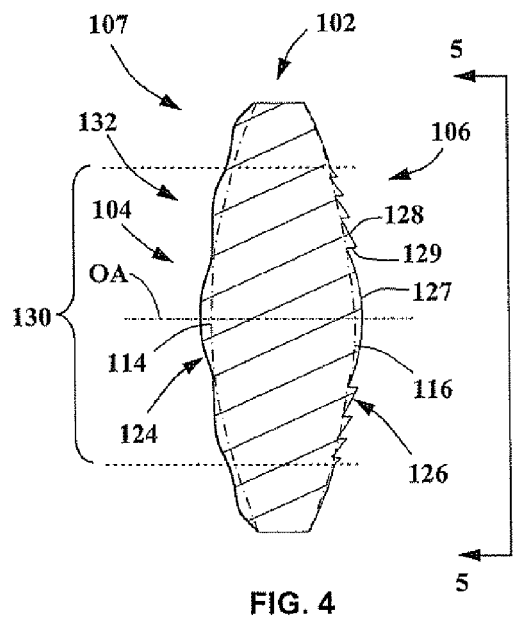
FIG. 4 is a side view of a cross-section of the intraocular lens shown in FIG. 2.
Figure 5:
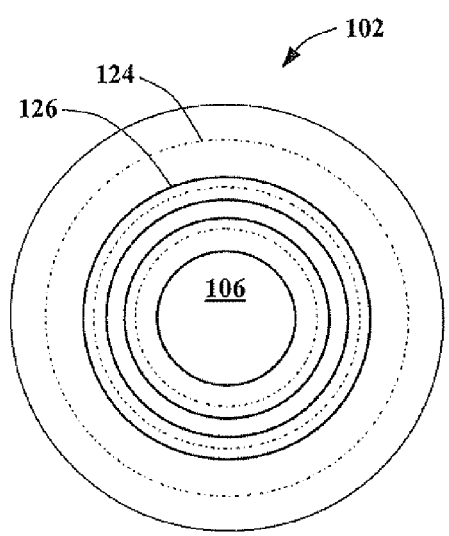
FIG. 5 is a plan view of the posterior surface of the intraocular lens shown in FIG. 4.

Referring to FIGS. 3-5, only the optic 102 of the intraocular lens 100 is shown (i.e., haptics 103 are not shown). The optic 102 comprises an anterior surface 104 and an opposing posterior surface 106. The optic 102 also has a clear aperture 107 disposed about the optical axis OA. The anterior surface 104 has an anterior base shape, figure, or curvature 114, while the posterior surface 106 has a posterior base shape, figure, or curvature 116. The base shapes 114, 116 provide a base optic 102 power that generally provides distant vision. The base optic 102 power is generally between −20 Diopters and +60 Diopters, typically between about +10 Diopters and about +40 Diopters.

The optic 102 also includes a multifocal refractive profile or element 124 imposed on, added to, or combined with the anterior base shape 114. In the illustrated embodiment, the refractive profile 124 is symmetrically disposed about the optical axis OA over a radial extent from the optical axis OA that includes the entire clear aperture 107 of the optic 102. Alternatively, the refractive profile 124 may be asymmetric disposed, may have a radial extent that is less than the entire clear aperture 107, and/or may have an inner radius that starts as a predetermined distance from the optical axis OA. The multifocal refractive profile 124 in FIGS. 3 and 4 is an undulating surface that has been exaggerated along the optical axis OA for illustrative purposes. In general, the local optical power of the multifocal refractive profile 124 is varied with radius from the optical axis OA by varying the local radius of curvature. The multifocal refractive profile 124 includes one or more portions having a base refractive power that is zero or about zero Diopter, or that has an average optical power that is zero or about zero Diopter. The multifocal refractive profile 124 also includes one or more portions having an add power or average add power that is added to the base refractive power, typically having a value of between about 1 Diopter and 4 Diopters. In some embodiments, the multifocal refractive profile 124 may include portions that have an add power or average add power that is negative, for example, about −1 Diopters.

Figure 6:
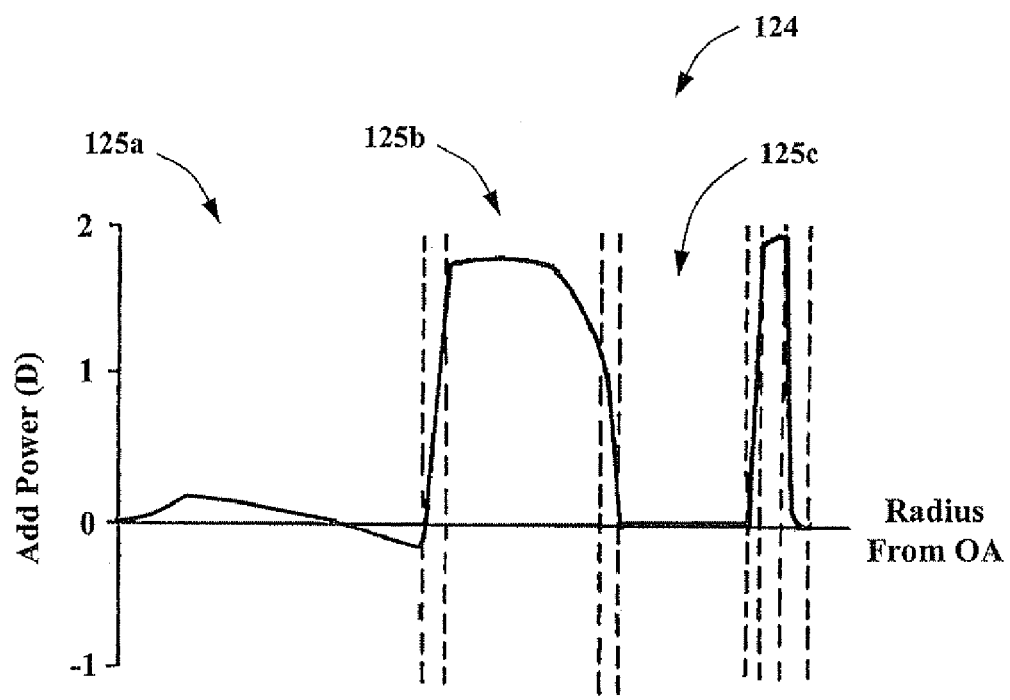
FIG. 6 is a plot of the refractive add power of a multifocal refractive profile for the intraocular lens shown in FIG. 5.

With additional reference to FIG. 6, the refractive profile 124 of the illustrated embodiment includes a portion 125a that has an average optical power of about zero Diopters. The multifocal refractive profile 124 also includes an portion 125b having an add power that varies continually with radius and having a maximum refractive add power of about 2 Diopters. The multifocal refractive profile 124 also includes a portion 125c having a constant power of zero Diopters, for example, to provide additional distant vision for larger pupil sizes or under scotopic lighting conditions.

The optic 102 further includes a multifocal diffractive profile or element 126 that is imposed on, added to, or combined with the posterior base shape 116. The multifocal diffractive profile 126 generally comprises a central echelette 127 surrounded by a plurality of annular echelettes 128, whereby the height of steps 129 between adjacent echelettes 127, 128 (exaggerated in FIGS. 3, 4 for illustrative purposes) and the shape of the echelettes 127, 128 are selected to provide constructive interference between echelettes for incident light on the optic 102 to produce two or more foci. The multifocal diffractive profile 126 may have, for visible light, a primary diffraction order, a secondary diffraction order, and a diffractive add power corresponding to a difference in optical power between the secondary diffraction order and the primary diffraction order. In some embodiments, the primary diffraction order is a zeroth diffraction order having an optical power of or about zero Diopters and the secondary diffraction order is a first diffraction order having diffractive optical power that is between about 2 Diopter and about 8 Diopters, so that the diffractive add power is equal to or approximately equal to the diffractive power of the second diffraction order. Alternatively, the primary diffraction order may be a first diffraction order of the diffractive profile 126 and the secondary diffraction order may be a second diffraction order of the diffractive profile 126 having an optical power that is between about 2 Diopter and 8 Diopters greater than the optical power of the primary diffraction order. In this case, the base power of the multifocal diffractive profile may be equal to the power of the primary diffraction order. In any event, the diffractive add power is generally within the range of about 2 Diopters to 8 Diopter, or between about 3 Diopters and about 4 Diopters. The latter range may correspond to both (1) a favorable amount of add power to provide near vision and (2) a degree of diffractive chromatic dispersion sufficient to reduce or eliminate a refractive chromatic aberration produced by the optic 102 and/or the cornea 14 of the eye 10. In certain embodiments, the diffractive add power is less than about 2 Diopter, for example, to provide an extended depth of focus, as disclosed in co-pending U.S. patent application Ser. No. 12/197,249, which is herein incorporated in its entirety.

The multifocal profiles 124, 126 may represent deviations from the base shapes 114, 116, respectively, these deviations providing the multifocal or other optical characteristics (e.g., chromatic correction characteristics) of the optic 102. As illustrated in FIGS. 3 and 4, the multifocal profiles 124, 126 may be added on top of the base shapes 114, 116. Alternatively, the base shapes 114, 116 may represent an average profile of the surfaces 104, 106, wherein the refractive profile 124 or the diffractive profile 126 represents deviations above and below this average surface profile.

The multifocal profiles 124, 126 have or provide an overlap portion 130 defining an overlap aperture or zone 132, which represents an aperture or zone over which light from an object or point source incident on the optic 102 passes through, and is acted upon by, both multifocal profiles 124, 126. Thus, light or a wavefront incident on the overlap aperture 132 is focused through interaction with both multifocal profiles 124, 126. In the illustrated embodiment, the overlap aperture 132 is filled by only a portion of the multifocal refractive profile 124 and by the entire the multifocal diffractive profile. The extent of the multifocal profiles 124 or 126 may be varied according to the requirements of a particular design or application. The overlap aperture 132 may be circular, as in the illustrated embodiment, or may be annular or some other shape.

Figure 7:
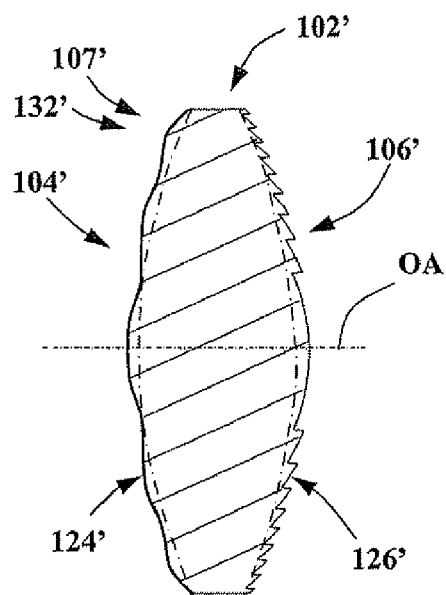
FIG. 7 is side view of a cross-section of a multifocal lens according another embodiment of the present invention.

Alternatively, as illustrated in FIG. 7, an optic 102' includes a multifocal refractive profile 124' and a multifocal diffractive profile 126' that both extend over the entire clear aperture 107' of the optic 102', wherein the overlap aperture 132' is equal to or substantially equal to the clear aperture 107'. In such embodiments, the multifocal diffractive profile 126' may be replaced by a monofocal diffractive profile, whereby the multifocality of the optic 102' is provided by the multifocal refractive profile 124'. The monofocal diffractive profile may be configured to correct or compensate for chromatic aberrations of the two or more foci provided by the multifocal refractive profile 124'. The corrected chromatic aberration may be that of the optic 102′ itself, or that of the combination of the optic 102′ and the eye 10 (e.g., of the cornea 14).

In general, light passing through the overlap aperture 132 has at least one combined add power produced by a combination of the refractive add power and the diffractive add power. Light passing through the overlap aperture may also have additional foci or add powers apart from combined add power. In the illustrate embodiment, for example, the multifocal diffractive profile 126 may be configured to split incident light between a zeroth diffraction order having zero optical power and a first diffraction order having 2 Diopters of optical power. As seen in FIG. 6, the base portion 125a of the multifocal refractive profile 124 has an average add power of about zero Diopters, while the add portion 125b of the multifocal refractive profile 124 has an add power of about 2 Diopters. Light passing through both the base portion 125a of the multifocal refractive profile 124 and the diffractive profile 126 is split into two foci, one with a power equal to the base optic 102 power (e.g., 20 Diopters based on the combined refraction of the base shapes 114, 116) and another with a refractive power equal to the base optic 102 power plus the 2 Diopters of diffractive add power provided by the first diffraction order. Light passing through the add portion 125b of the multifocal refractive profile 124 and the multifocal diffractive profile 126 is split into two foci, one with approximately 2 Diopters of add power plus the base optic 102 power and another with about 4 Diopters of add power plus the base optic 102 power (the about 4 Diopters coming from about 2 Diopters of refractive power from the add portion 125b and 2 Diopters of diffractive add power from the first diffraction order). Thus, in this example, the optic 102 over the overlap aperture 132 to advantageously provides at least three foci when the base optic 102 power produced by the base shapes 114, 116 is included (e.g., 20 Diopters, 22 Diopters, and 24 Diopters, for a base optic 102 power of 20 Diopters, a multifocal refractive add power of about 2 Diopters, and a multifocal diffractive add power of 2 Diopters). The combination of refractive and diffractive add powers may be advantageously configured to reduce halo effects or to otherwise utilize the distinct advantages of each type (refractive or diffractive) multifocal profile or element. For example, the diffractive profile may be configured to provide a predetermined relationship between the amount of light energy, power, or intensity in near and distant foci that is independent of the area or diameter of pupil size or lighting conditions.

In some embodiments, the refractive add power is between about 1 Diopter and about 3 Diopters and the diffractive add power is between about 1 Diopter and about 3 Diopters. The optic 102 may have a total add power within the overlap aperture 132 that is between about 3.5 Diopter and about 4.5 Diopters. In some embodiments, the diffractive add power and/or the refractive add power is selected to provide intermediate vision, while the total add power (the combination of the diffractive and refractive add powers) is able to provide near vision.

In the illustrated embodiment, the multifocal refractive profile 124 is disposed on an optic 102 surface opposite that on which the multifocal diffractive profile 126 is disposed; however, both profiles 124, 126 may be disposed on a common surface. For example, the both profiles 124, 126 may be both be imposed on either the anterior shape 114 or the posterior shape 116. Other variations from the design shown in FIGS. 3-6 are also anticipated. For example, the multifocal refractive profile 124 may be disposed on the posterior base shape 116 and/or the multifocal diffractive profile 126 may be disposed on the anterior base shape 114. In general, the optic may comprise other refractive and/or diffractive profiles in addition to the profiles 124, 126, wherein one or more of the refractive profiles define one or more overlap portions, zones, or apertures with one or more of the diffractive profiles.

The general shape of the optic 102, as defined by the base shapes 114, 116, may be biconvex, plano-convex, plano-concave, meniscus, or the like. The optic 102 may include a Fresnel surface or profile. In certain embodiments, the base shapes 114, 116, or portions thereof, are spherical and each shape 114, 116 or portion thereof is characterized by radius of curvature. In such embodiments, a base optic 102 power is determinable based on the radius of curvature of each shape 114, 116 or portion thereof, the refractive index of the optic 102 material, and the refractive index of the media into which the intraocular lens 100 is placed. In some embodiments, one or both the shapes 114, 116 may be aspheric, for example to correct, cancel, or at least partially compensate for a spherical aberration of the eye 10 (e.g., the cornea 14) and/or the optic 102. In such embodiments, the aspheric surface may be characterized by an equation for a conic section containing a radius of curvature and/or a conic or asphericity constant over all or a portion of the optic shape or surface. For example, in certain embodiments, one or both base shapes 114, 116 of the optic 102 may have a shape or profile that is represented by a so-called sag Z given by the equation:

$$Z(r) = \frac{r^2/R}{1 + \sqrt{1 - r^2(CC+1)/R^2}} \quad (1)$$

where r is a radial distance from the center or optical axis of the lens, R is the radius or curvature at the center of the lens, CC is the so-called conic constant. This equation may represent the sag Z over an entirety of one or both base shapes 114, 116, or over a particular zone, annular region, or some other shaped region of the base shapes 114, 116.

In certain embodiments, the one or both base shapes 114, 116 are characterized by an equation for a conic section and one or more higher order polynomials in radius from the optical axis over all or a portion of the optic surface. Examples of such aspheric shapes are disclosed in U.S. Pat. Nos. 6,609,793; 6,830,332; 7,350,916 to Hong et al.; and US Patent Application No. 2004/0156014, all of which are herein incorporated by reference. For example, one or both base shapes 114, 116 may have a base shape or profile represented by sag Z given by an equation:

$$Z(r) = \frac{r^2/R}{1 + \sqrt{1 - r^2(CC+1)/R^2}} + ADr^4 + AEr^6 + \ldots \quad (2)$$

where r is a radial distance from the center or optical axis of the lens, R is the radius of curvature at the center of the lens, CC is a conic constant, and AD and AE are polynomial coefficients additional to the conic constant CC. This equation may represent the sag Z over an entirety of one or both base shapes 114, 116, or over a particular zone, annular region, or some other shaped region of the base shapes 114, 116.

One or both base shapes 114, 116 of the optic 102 may have a shape or curvature that is represented by an equation containing one or more coefficients for other types of polynomial equations, such as a Zernike polynomial, a Fourier polynomial, or the like. One or both base shapes 114, 116, may also be non-symmetric, for example, having a toric shape for correcting an astigmatism of the cornea 14. In addition, the one or both base shapes 114, 116 of the optic 102 may be segmented, for example, comprising segmented annular segments described by different equations or different coefficient values. In such embodiments, the segments may be joined together as a spline.

An aspheric shape of one or both base shapes 114, 116 of the optic 102 may be configured to produce an aberration, for example to counteract, reduce, or eliminate one or more aberrations of the optic 102 and/or eye 10 (e.g., the cornea 14). In some embodiments, the aspheric shape is configured to counteract, reduce, or eliminate aberrations introduced into an incident wavefront, for example, into a wavefront from a collimated wavefront, a distant point source, and/or the cornea 14 of the eye 10. The aberration produced or corrected by the optic 102, or some zone or portion thereof, may be astigmatism or a spherical aberration. Additionally or alternatively, the aberration produced or corrected by the optic 102, or some zone or portion thereof may be a chromatic aberration or a higher order monochromatic aberrations such as coma, trefoil, or the like.

The intraocular lens 100 may be configured for insertion into or in front of the capsular bag 20. Alternatively, the intraocular lens 100 may be configured to be located in the anterior chamber in front of the iris 26. In addition, the optic 102 or the intraocular lens 100 may be configured to be an add-on or piggy-back lens that is used to supplement a second intraocular lens or optic.

The optic 102 or the intraocular lens 100 may be configured to provide accommodation. For example, the optic 102 may be made from a relatively soft material and sized to fill capsular bag 20. Alternatively, the optic 102 may be attached to haptics or an optic positioning element that either moves the optic 102 along the optical axis OA and/or changes shape in response to an ocular force produced by a ciliary muscle, zonules, and/or a capsular bag. In such embodiments, the optic 102 may be combined with one or more additional optics. The accommodating intraocular lens may additionally or alternatively provide accommodation by axial rotation of the optic or based on the so-called Alvarez principle (e.g., based on translation of the optic either axially or transversely).

In certain embodiments, the multifocal diffractive profile 126 of the optic 102 may be replaced by, or supplemented by, a monofocal diffractive profile. The monofocal diffractive profile may be configured to have only one diffraction order in the visible band that produces or provides a focus. Alternatively, the monofocal diffractive profile may be configured to have a high MOD profile, whereby a plurality of diffraction orders of the monofocal diffractive profile focus light at different wavelengths to a single focus or substantially a single focus (e.g., as disclosed in U.S. Pat. No. 7,093,938 to Morris).

The multifocal refractive profile 124 may provide a relatively low amount of add power, for example, within a range of about 1 Diopter to about 2 Diopter (e.g., to provide distant and intermediate vision). Alternatively, the multifocal refractive profile 124 may include portions that provide a relatively high add power, for example, having an optical power from about 3 Diopter to about 4 Diopter (e.g., to provide distant and near vision) or from about 3 Diopters to about 6 Diopters. The monofocal diffractive profile may be disposed on the same surface or opposite surface as the multifocal refractive profile 124. One advantage of the combination of a monofocal diffractive profile in combination with a multifocal refractive profile is that all the foci of the lens or optic have the same or similar amounts of correction for chromatic aberrations. In some embodiments, an optic or lens comprises both a monofocal diffractive profile and a multifocal diffractive profile, wherein the profiles are contained on the same or opposite surfaces. In such embodiments, one or both diffractive profiles have an aperture that is less than the clear aperture of an optic or lens.

The profiles 124, 126 may be machined or cast to form the surfaces 104, 106 using conventional techniques know in the art. The spacing and shape of the echelettes of the diffractive profile 126 are generally according to those known within the art for forming monofocal, bifocal, or multifocal diffractive intraocular lenses, contact lenses, or the like; for example, as disclosed in various patents to Allen Cohen, Michael Freeman, John Futhey, Patricia Piers, Chun-Shen Lee, Michael Simpson, and others. The profiles 124, 126 may be a physical profile, as illustrated in FIGS. 3 and 4. Alternatively, one or both of the profiles 124, 126 may be replaced or supplemented by a gradient index within the optic 102 that is configured to provide the same or a similar refractive and/or diffractive effect to that produced by the profiles 124, 126.

The intraocular lens 100, as well as other intraocular lenses discussed herein, may be constructed of any of the various types of material known in the art. For example, the intraocular lenses according to embodiments of the present invention may be a foldable lens made of at least one of the materials commonly used for resiliently deformable or foldable optics, such as silicone polymeric materials, acrylic polymeric materials, hydrogel-forming polymeric materials (e.g., polyhydroxyethylmethacrylate, polyphosphazenes, polyurethanes, and mixtures thereof), and the like. Other advanced formulations of silicone, acrylic, or mixtures thereof are also anticipated. Selection parameters for suitable lens materials are well known to those of skill in the art. See, for example, David J. Apple, et al., Intraocular Lenses: Evolution, Design, Complications, and Pathology, (1989) William & Wilkins, which is herein incorporated by reference. The lens material may be selected to have a relatively high refractive index, and thus provide a relatively thin optic, for example, having a center thickness in the range of about 150 microns to about 1000 microns, depending on the material and the optical power of the lens. At least portions of the intraocular lens, for example one or more haptics or fixation members thereof, may be constructed of a more rigid material including such polymeric materials as polypropylene, polymethylmethacrylate PMMA, polycarbonates, polyamides, polyimides, polyacrylates, 2-hydroxymethylmethacrylate, poly(vinylidene fluoride), polytetrafluoroethylene and the like; and metals such as stainless steel, platinum, titanium, tantalum, shape-memory alloys, e.g., nitinol, and the like. In some embodiments, the optic and haptic portions of the intraocular lens are integrally formed of a single common material.

In the illustrated embodiments of FIGS. 3-7, optics 102, 102' are configured so the light incident on at least portions thereof (specifically on the overlap aperture 132) interact with two multifocal profiles (profiles 124, 126 or profiles 124', 126'). In certain embodiments, it may be beneficial to configure various multifocal profiles (refractive and diffractive) such that light incident upon some or all sub-apertures of the optic generally interacts with only a single multifocal profile at a time (either refractive or diffractive).

Figure 8:
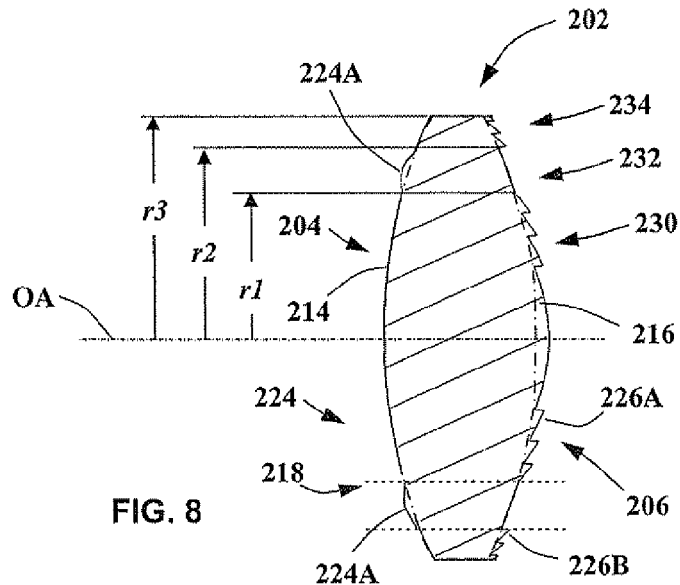
FIG. 8 is a side view of a cross-section of a multifocal lens according to yet another embodiment of the present invention.

For example, referring to FIG. 8, in certain embodiments an optic 202 includes an anterior surface 204 and an opposing posterior surface 206, where the anterior surface 204 has an anterior shape, figure, or curvature 214 and the posterior surface 206 has a posterior shape, figure, or curvature 216, wherein the shapes 214, 216 together provide a base optic 202 power. The optic 202 includes an inner or central zone 230 disposed about an optical axis OA extending out to a radius r1, an intermediate zone 232 disposed about the inner zone 230 extending over a range from r1 to r2, and an outer zone 234 disposed about the intermediate zone 232 extending over a range from r2 to r3. The inner zone 230 is circular when viewed from a front view of the optic 202, while the zones 232, 234 are annular; however, other shapes are possible (e.g., the inner zone 230 may also be annular, or any of the zones may be oval or some other shape). As used herein, a "zone" of an optic includes any features of, or between, the anterior and posterior surfaces 204, 206 located within the radial boundaries of the zone relative to an optical axis (e.g., in the case of an annular zone, between inner and outer radii from an optical axis of an optic).

The optic 202 also includes a first diffractive profile 226A imposed on the posterior shape 216 and located within the inner zone from the optical axis OA out to radius r1. The optic 202 also includes a second diffractive profile 226B imposed on the posterior shape 216 and located within the outer zone 234 from radius r2 out to radius r3. The optic 202 additionally includes a multifocal refractive profile 224 that is imposed on the anterior shape 214 and includes a refractive add portion 224A having refractive add power. The refractive add portion 224A is radially disposed intermediate the diffractive profile 226A, 226B and within the intermediate zone 232 and has a radial extent from r1 to r2

Either or both the diffractive profiles 226A, 226B may have, for visible light, a primary diffraction order having a first diffraction power, a secondary diffraction order having a second diffraction power, and an add power corresponding to a difference between the first and second diffraction powers. In some embodiments, at least one of the diffractive profiles 226A, 226B is a monofocal diffractive profile having only a single diffraction order producing a focus within the visible band of the electromagnetic spectrum, for example, to correct or compensate for a chromatic aberration or dispersion produced by the optic 202 and/or the cornea 14 of the eye 10.

Figure 9:
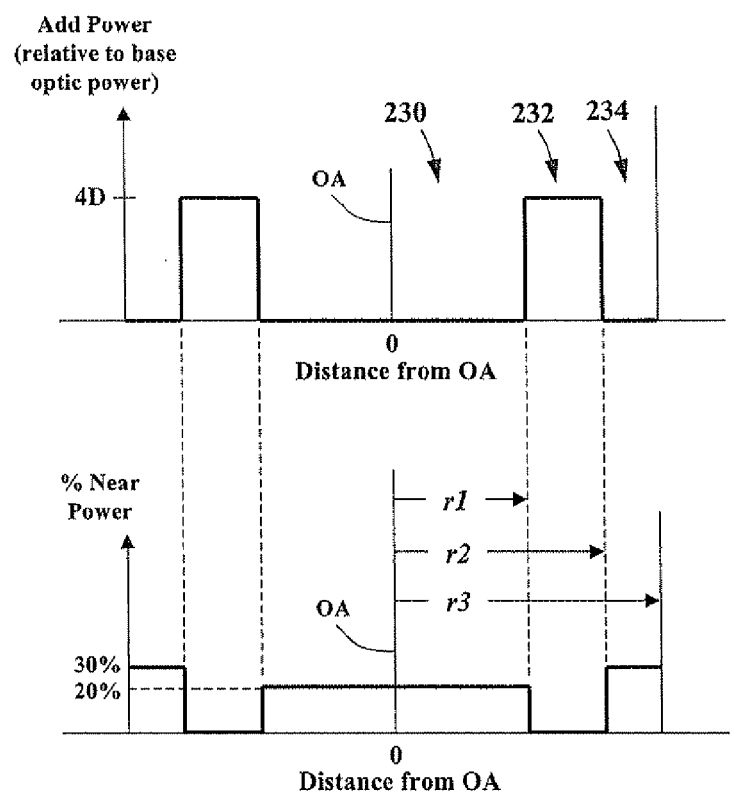
FIG. 9 is a plot of refractive and diffractive characteristics of the multifocal lens shown in FIG. 8.

The diffractive profiles 226A, 226B and/or the multifocal refractive profile 224 may be located on either the anterior or posterior surfaces 204, 206. In the illustrated embodiment, the diffractive profiles 226A, 226B are both disposed on the posterior surface 206, while the refractive profile 224, specifically the refractive add portion 224A, is disposed on the opposite surface 204. Alternatively, one or both diffractive profiles 226A, 226B may be disposed on a common surface (e.g., the surface 204 or 206) with the refractive add portion 224A. The zones 230, 232, 234, as defined by the diffractive profiles 226A, 226B and refractive add portion 224A, are generally adjacent to one another and may be configured to form contiguous surface or volume elements. In some embodiments, the optic 202 includes transition zones disposed between one or more sets of adjacent zones (e.g., between zones 230, 232 and/or between zones 232, 234). As such, transition zone surfaces may be configured to provide a smooth blending of the surface portions between adjacent primary zones. For example, if the profiles 224, 26A, 226B are on a single surface (surface 204 or 206), a transition zone surface between adjacent profiles may be configured to blend these surface portion and/or to reduce glare that could be created by discontinuities or sharp borders at a junction between adjacent profiles. The anterior and/or posterior surfaces 204, 206 over one or more adjacent zones may be defined, in whole or in part, by one or more splines. Referring again to FIG. 8, the refractive add portion 224A is radially disposed between the diffractive profiles 226A, 226B. The refractive add portion 224A may have a constant add power between r1 and r2, as illustrated in FIG. 9. Alternatively, the refractive add portion 224A may have an add power that varies between r1 and r2, for example, to provide multiple foci, an extended depth of focus, and/or both near vision and some intermediate vision (e.g., with an add power of about 3 Diopter to about 4 Diopters for near vision, and an add power of about 1 Diopter to about 2 Diopters for intermediate vision). The refractive add portion 224A may have a refractive add power that is equal to or substantially equal to the diffractive add power of the first and/or second diffractive profile 226A, 226B, for example, about 3 Diopters to about 4 Diopters. Alternatively, the refractive add portion 224A may have a refractive add power that is less than that of the diffractive add power of the first and/or second diffractive profile 226A, 226B (e.g., to provide intermediate vision under mesopic or photopic lighting conditions, for example, to allow a subject to focus on a computer monitor under typical room lighting conditions). In some embodiments, the multifocal refractive profile 224 includes a base power that is zero or about zero, and includes one or more add powers for intermediate vision or near vision (e.g., about 1 Diopter, about 2 Diopter, about 3 Diopters, or about 4 Diopters).

In certain embodiments, the intermediate zone 232 has a constant refractive optical power that is equal to a base power of the optic 202, for example, so that the intermediate zone 232 provides distant vision. In such embodiments, the multifocal refractive profile 224 includes a zone or surface portion having an add power, for example, to provide near or intermediate vision. In one such embodiment, multifocal refractive profile 224 include an add power for intermediate vision in the inner zone 230 and/or the outer zone 234, wherein the multifocal diffractive profile 226A and/or 226B is (are) configured to provide intermediate and near vision. In other embodiments, the multifocal refractive profile 224 is replaced with a monofocal refractive profile having a constant refractive optical power, whereby the multifocal diffractive profiles 226A, 226B are radially separated by a zone of constant refractive optical power for distant vision and no diffractive optical power. The monofocal refractive profile may comprise a spherical surface having a constant radius of curvature or may comprise an aspheric surface, for example, having a spherical aberration configured to correct or reduce a spherical aberration of the optic 202 and/or the eye 10.

The diffractive profiles 226A, 226B and the refractive add portion 224A may advantageously be configured to vary add power with radius from the optical axis OA, both in terms of magnitude and type of focusing produced (e.g., either diffractive or refractive). For example, it has been found that the combination of a multifocal diffractive pattern in inner zone 230 and a refractive add or multifocal profile in more peripheral regions (e.g., the intermediate zone 232) can offer distinct benefits, such as the ability to reduce halo effects (e.g., as disclosed in U.S. Pat. No. 7,188,949 to Bandhauer), and more flexibility in distributing the light energy, power, or intensity in the near, intermediate, and far foci as the pupil diameter increases. For example, a design may utilize the principle that the amount of light energy, power, or intensity from a near focal point going into a particular halo or halo element depends on area, in the case of a multifocal refractive profile, but depends on echelette step height and/or shape in the case of a multifocal diffractive profile.

The diffractive profiles 226A, 226B may be configured to have the same or similar optical characteristics. For example, the diffractive profiles 226A, 226B may both be monofocal profiles having the same or different diffractive optical powers. Alternatively, one or both of the diffractive profiles 226A, 226B may be multifocal profiles, wherein the each profile 226A, 226B has the same diffractive optical power(s) (e.g., the same base power and/or add power).

In certain embodiments, the diffractive profiles advantageously have different optical characteristics. For example, one of the profiles 226A, 226B may be a monofocal profile, while the other is a multifocal profile. In other embodiments, each of the profiles 226A, 226B is a monofocal profile, but the diffractive optical power of each profile is different (e.g., one configured to provide distant vision and the other to provide intermediate or near vision). In yet other embodiments, each of the profiles 226A, 226B is a multifocal profile, with each having a different optical characteristic. For example, the profiles 226A, 226B may have different diffraction efficiencies, different base or add powers, different design wavelengths, and/or different echelette step heights and/or echelette shapes.

Referring further to FIG. 9, a preferred embodiment of the profiles 224, 226 is illustrated in which the profiles are configured to have different optical characteristic in the form of different diffraction efficiencies. The lower plot of FIG. 9 shows the diffraction efficiency of the diffractive profiles 226A, 226B as a function of distance from the optical axis OA, while the upper plot shows the add power of the multifocal refractive profile 224 as a function of the distance from the optical axis OA. The scale of the horizontal axis of each plot in FIG. 9 is the same, allowing comparison of the refractive add power and diffraction efficiency at various distances from the optical axis OA. The diffraction efficiency of the diffractive profile 226A is 20%, from the optical axis out to the radius r1, while the refractive power of the multifocal refractive profile 224 is zero. Thus, within the inner zone 230, the optic 202 has a base optic power provided by the combination of the anterior and posterior shapes 214, 216, and a diffractive add power provided by the first diffractive profile 226A, with approximately 20% of the useful light energy, power, or intensity from light at the design wavelength going to the diffractive add power (e.g., for providing near or intermediate vision) and approximately 80% of the useful light energy, power, or intensity going into the base optic power (e.g., for providing distant vision). The add power of the multifocal diffractive profile may be between about 2 Diopters and about 4 Diopters, although other diffractive add powers are possible (e.g., between about 1 Diopter and about 2 Diopters for providing intermediate vision and/or for providing an enhanced depth of focus). It will be understood by those of skill in the art that some light at the design wavelength and at other wavelengths will be directed into other diffraction orders that are different from the primary and secondary diffraction orders, the amount of light directed into higher and/or lower diffraction order depending on the specific design of the first diffractive profile 226A.

Since there is not a diffractive grating or profile within the intermediate zone 232 in the illustrated embodiment, there is no add power due to diffraction; however, between r1 and r2 the multifocal refractive profile 224 includes the refractive add portion 224A which, in the illustrated embodiment, provides a refractive add power of 4 Diopters, which is sufficient to provide near vision. Thus, for medium pupil sizes (e.g., about 3 mm diameter) the optic 202 provides both a diffractive add power and a refractive add power. In some embodiments, the diffractive add power is also 4 Diopters and the optic 202 has two foci, one corresponding to the base optic 202 power and one corresponding to an add power that is produced by both the diffractive profile 226A and the refractive add portion 224A. Alternatively, the refractive add portion 224A may be or include a refractive add power that is less than the diffractive add power, for example, a refractive add power configured to provide intermediate vision or a different amount of near vision (e.g., about 1 Diopter, about 2 Diopters, or about 3 Diopters). In other embodiments, the refractive add portion 224A may include at least two refractive add powers, and/or a continually and/or monotonically varying add power (e.g., of about 3 Diopter and about 4 Diopter; or continually increasing or decreasing from about 2 Diopters to about 3 Diopters or about 4 Diopters).

Between the radii r2 and r3 of the illustrated embodiment for the optic 202, the multifocal refractive profile 224 again has no add power, while the second diffractive profile 226B provides a diffractive add power. The profile 226B is configured to produce a 30% diffraction efficiency, wherein 30% of the useful light energy, power, or intensity at the design wavelength goes into providing a diffractive add power (e.g., for near or intermediate vision) and approximately 70% of the useful light energy, power, or intensity going into a base optic power (e.g., for distant vision). In some embodiments, the diffractive add power of the second diffractive profile 226B is the same as the diffractive add power of the first diffractive profile 226A and/or is the same as the refractive add power provided by the refractive add portion 224A. In some embodiments, the add powers of the zones 230, 232, 234 are each different, for example, to provide an extended depth of focus for large pupil diameters, to provide a predetermined distribution of light energy, power, or intensity between foci for given pupil diameter, or provide a predetermined light energy, power, or intensity distribution within halos to reduce the effect thereof on a subject.

The effects of halos may be reduced by configuring the first and/or second diffractive profiles 226A, 226B to have diffraction efficiencies of less than 50%. One advantage of using a lower diffraction efficiency is that both the amount and distribution of light within halos produced by the multifocal optic 202 may result in reduced halo effects. In some embodiments, the diffraction efficiency is between 10% and 40%, or between 15% and 35%. For example, in the illustrated embodiment, the diffraction efficiency of the first diffractive profile 226A is between 15% and 25%, while the diffraction efficiency of the second diffractive profile 226B is between 25% and 35%. In the illustrated embodiment shown in FIG. 9, certain advantages in terms of halo effects may be provided by configuring the diffraction efficiency of the second diffractive profile 226B (disposed in the outer zone 234) to be greater than the diffraction efficiency of the first diffractive profile 226A (disposed in the inner zone 230). In other embodiments, the diffraction efficiency of the second diffractive profile 226B is less than the diffraction efficiency of the first diffractive profile 226A.

In certain embodiments, the diffraction efficiency of one or both the diffractive profiles 226A, 226B are relatively high, for example, about 50%, between about 40% and about 60%, or even greater than 60%. For example, the diffractive profile 226A may be relatively high so that a significant amount of near vision is provided for a relatively small pupil (e.g., having a diameter from about 2 mm to about 3 mm). In such embodiments, or in other embodiments, the refractive add power of the refractive add portion 224A may be relatively small (e.g., between about 1 Diopter and about 2 Diopters) or may be zero or about zero (e.g. providing only distant vision).

Other variations of the profiles shown in FIGS. 8 and 9 are anticipated. For example, inner and/or outer zones 230, 234 may contain a refractive profile in addition to, or in place of, the diffractive profiles 226A, 226B. In addition, the intermediate zone 232 may contain a diffractive profile in addition to, or in place of, the refractive add portion 224A. In certain embodiments, the zones 230, 232, 234 fill the entire clear aperture of the optic 202. In other embodiments, the optic 202 includes other multifocal diffractive and/or multifocal refractive zones, for example, within the inner zone 230 or outside the outer zone 234. In certain embodiments, the refractive add portion 224A has a relatively low add power (e.g., between about 1 Diopter and about 2 Diopters), or even a negative add power (e.g., less than a base power of the refractive profile 224). In such embodiments, the intermediate zone containing the refractive add portion 224A may also include a multifocal or monofocal diffractive profile, either on the same surface or opposite surface containing the refractive add portion 224A.

In a preferred embodiment, one of the diffractive profiles 226A, 226B is a monofocal diffractive profile and the other profile 226A, 226B is a multifocal diffractive profile. For example, the optic 202 may advantageously be configured so that the inner diffractive profile 226A is a multifocal diffractive profile, the intermediate refractive add portion 224A is multifocal refractive profile, and the outer diffractive profile 226B is a monofocal diffractive profile. In this embodiment, when the pupil size is smaller (e.g., under photopic lighting conditions), the multifocal diffractive profile 226A provides power for both far focus and near focus that is relatively distinct and sharp as compared to a refractive multifocal. Under such conditions, it has been found that there is less need to provide intermediate vision, since smaller pupil sizes inherently have relatively large depths of focus. Under mesopic lighting conditions, a multifocal refractive profile 224A favorably provides advantages such as the ability of provide at least some intermediate vision, reduced halo effects, and/or more flexibility in distributing the amount of light energy, power, or intensity in the near, intermediate, and far foci as the pupil diameter increases. The outer monofocal diffractive profile 226B corrects or reduces chromatic aberrations and provides more distant vision for larger pupil sizes, for example, to provide better distant vision during night time driving. Alternatively, the outer monofocal diffractive profile 226B may be configured to provide near or intermediate vision.

The anterior and/or posterior shapes 214, 216, or portions thereof, may be either spherical or aspheric, for example, comprising a shape described by Equations 1 and 2 above, or described by a Zernike polynomial, Fourier polynomial, or the like, One or both base shapes 214, 216, may also be non-symmetric, for example, having a toric shape for correcting an astigmatism of the cornea 14. In certain embodiments, one or both shapes 214, 216 may be segmented or splined. For example, since spherical aberrations are generally less at smaller radii from the optical axis, the shapes 214, 216 of the inner zone 230 and/or the intermediate zone 232 may be characterized by a sphere with a constant radius of curvature, while the shape 214 and/or shape 216 within the outer zone 234 is characterized by a polynomial equation such as Equation 1 or 2 above.

In certain embodiments, the optic 202 may comprise additional zones besides the zones 230, 232, 234, for example, comprising 4 zones, 5 zones, or 6 zones in total. In such embodiments, a first set of alternating zones may contain monofocal and/or multifocal diffractive profiles that are imposed on a base shape, while a second set of alternating zones may contain multifocal refractive profiles that are imposed on a base shape (either on the same or opposite surface of the optic). Alternatively, two (or more) adjacent zones may both (all) contain either a multifocal refractive profile, a multifocal diffractive profile, or a monofocal diffractive profile. In some embodiments, one or more of the zones is a monofocal zone providing a single focus or optical power (e.g., for providing near, intermediate, or distant vision), while one or more of the remaining zones include a multifocal refractive profile and/or a multifocal diffractive profile. In any of these embodiments, one or both surfaces 204, 206 may contain a monofocal diffractive profile or grating over all or a portion of one of the surfaces 204, 206 that is configured to have only one focus at a design wavelength within the visible light band of the electromagnetic spectrum (e.g., to correct or compensate for a chromatic aberration of the optic 202 or the eye 10).

In general, any of feature, properties, or fabrication methods discussed above regarding the optics 102, 102' may be incorporated, where applicable, into the optic 202, or visa versa. For example, any features of the shapes, surfaces, or profiles discussed in relationship to the optics 102, 102' may be incorporated, where applicable, into the optic 202, or visa versa.

The above presents a description of the best mode contemplated of carrying out the present invention, and of the manner and process of making and using it, in such full, clear, concise, and exact terms as to enable any person skilled in the art to which it pertains to make and use this invention. This invention is, however, susceptible to modifications and alternate constructions from that discussed above which are fully equivalent. Consequently, it is not the intention to limit this invention to the particular embodiments disclosed. On the contrary, the intention is to cover modifications and alternate constructions coming within the spirit and scope of the invention as generally expressed by the following claims, which particularly point out and distinctly claim the subject matter of the invention.

What is claimed is:

1. An ophthalmic lens, comprising:
an optic comprising a first surface having a first shape and an opposing second surface having a second shape, the shapes together providing a base optic power;
an inner zone disposed about an optical axis, an intermediate zone disposed about the inner zone, and an outer zone disposed about the intermediate zone;
a first diffractive profile imposed on one of the shapes and radially disposed within the inner zone;
a second diffractive profile imposed on one of the shapes and radially disposed within the outer zone;
a multifocal refractive profile imposed on one of the shapes and including a refractive portion radially disposed within the intermediate zone, the multifocal refractive profile including an add portion having refractive add power;
wherein the first diffractive profile and the second diffractive profile are both multifocal diffractive profiles having, for visible light, a primary diffraction order, a secondary diffraction order, and a diffractive add power corresponding to a difference in optical power between the secondary diffraction order and the primary diffraction order;
wherein the secondary diffraction order of the second diffractive profile has a diffraction efficiency at a visible light design wavelength that is greater than the secondary diffraction order of the first diffractive profile at the design wavelength;
wherein the diffraction efficiency at a visible light design wavelength of the secondary diffraction order of the first diffractive profile is between 15 percent and 25 percent and the remaining diffraction efficiency of the first diffractive profile is with the primary diffraction order of the first diffractive profile; and
wherein the diffraction efficiency at a visible light design wavelength of the secondary diffraction order of the second diffractive profile is between 25 percent and 35 percent and the remaining diffraction efficiency of the second diffractive profile is with the primary diffraction order of the second diffractive profile.

2. The ophthalmic lens of claim 1, wherein the zones are contiguous.

3. The ophthalmic lens of claim 1, further comprising a transition zone disposed between at least one of (1) the inner zone and the intermediate zone and (2) the intermediate zone and the outer zone.

4. The ophthalmic lens of claim 1, wherein the refractive profile includes a base portion having a base refractive power of about zero Diopters.

5. The ophthalmic lens of claim 1, wherein the optical axis passes through the inner zone.

6. The ophthalmic lens of claim 1, wherein at least one of the diffractive profiles is imposed on the first shape and the refractive profile is imposed on the second shape.

7. The ophthalmic lens of claim 1, wherein all the profiles are all imposed on only one of the shapes.

8. The ophthalmic lens of claim 1, wherein the first diffractive profile is disposed on a surface opposite the second diffractive profile.

9. The ophthalmic lens of claim 1, wherein the primary diffraction order of the first and second diffractive profile is a zeroth diffraction order having an optical power of about zero Diopters and the secondary diffraction order of the first and second diffractive profile is a first diffraction order having an optical power that is between about 2 Diopters and about 8 Diopters.

10. The ophthalmic lens of claim 1, wherein the primary diffraction order of the first and second diffractive profile is a first diffraction order, the secondary diffraction order of the first and second diffractive profile is a second diffraction, and the add power is between about 2 Diopter and about 8 Diopters.

11. The ophthalmic lens of claim 1, wherein the diffractive add power of the first and second diffractive profile is between about 3 Diopters and about 6 Diopters.

12. The ophthalmic lens of claim 1, wherein the diffractive add power of the first and second diffractive profile is less than about 2 Diopters.

13. The ophthalmic lens of claim 1, wherein the refractive add power is between 1 Diopter and about 4 Diopters.

14. The ophthalmic lens of claim 1, wherein the refractive add power is equal to the diffractive add power.

15. The ophthalmic lens of claim 1, wherein at least one of the shapes is characterized over at least one of the zones by an equation having an asphericity constant, an equation having a higher order polynomial in radius from the optical axis, or an equation having both an asphericity constant and a higher order polynomial in radius from the optical axis.

16. The ophthalmic lens of claim 1, wherein at least one of the zones has a negative spherical aberration.

17. The ophthalmic lens of claim 1, wherein at least one of the zones includes a monofocal diffractive profile imposed on at least one of the shapes.

18. The ophthalmic lens of claim 1, further comprising an additional zone having a multifocal profile, wherein the multifocal profile is a multifocal refractive profile or a multifocal diffractive profile.

19. The ophthalmic lens of claim 18, wherein the additional zone is radially disposed outside the inner zone, outside the intermediate zone, or outside the outer zone.

20. The ophthalmic lens of claim 1, wherein the first diffractive profile has a first optical characteristic, and the second diffractive profile has a second optical characteristic that is different from the first optical characteristic.

21. The ophthalmic lens of claim 20, wherein the first optical characteristic is a first diffractive add power and the second optical characteristic is a second diffractive add power, the first and second diffractive add powers differing by at least 0.25 Diopters.

22. The ophthalmic lens of claim 20, wherein the first optical characteristic is a first step height of echelettes within the inner zone and the second optical characteristic is a second step height of echelettes within the outer zone, the first and second step heights being different.

23. The ophthalmic lens of claim 20, wherein the first optical characteristic is a first chromatic dispersion and the second optical characteristic is a second chromatic dispersion, the first and second chromatic dispersions being different.

24. The ophthalmic lens of claim 1, wherein at least one of the diffractive profiles comprises a plurality of echelettes, each of the echelettes having a different step height, the step heights progressively decreasing with increasing radial distance from the optical axis.

25. An ophthalmic lens, comprising:
an optic comprising a first surface having a first shape and an opposing second surface having a second shape, the shapes together providing a base optic power;
an inner zone disposed about an optical axis, an intermediate zone disposed about the inner zone, and an outer zone disposed about the intermediate zone;
a first diffractive profile imposed on one of the shapes and radially disposed within the inner zone;
a second diffractive profile imposed on one of the shapes and radially disposed within the outer zone;
a refractive profile imposed on one of the shapes and including a refractive portion radially disposed within the intermediate zone;
wherein the first diffractive profile and the second diffractive profile are both multifocal diffractive profiles having, for visible light, a primary diffraction order, a secondary diffraction order, and a diffractive add power corresponding to a difference in optical power between the secondary diffraction order and the primary diffraction order;
wherein the secondary diffraction order of the second diffractive profile has a diffraction efficiency at a visible light design wavelength that is greater than the secondary diffraction order of the first diffractive profile at the design wavelength;
wherein the diffraction efficiency at a visible light design wavelength of the secondary diffraction order of the first diffractive profile is between 15 percent and 25 percent and the remaining diffraction efficiency of the first diffractive profile goes to the primary diffraction order of the first diffractive profile; and
wherein the diffraction efficiency at a visible light design wavelength of the secondary diffraction order of the second diffractive profile is between 25 percent and 35 percent and the remaining diffraction efficiency of the second diffractive profile goes to the primary diffraction order of the second diffractive profile.

26. The ophthalmic lens of claim 25, wherein the lens includes a multifocal refractive profile imposed on one of the shapes.

27. The ophthalmic lens of claim 25, wherein the refractive profile has a refractive optical power equal to the base optic power.

28. An ophthalmic lens, comprising:

an optic comprising a first surface having a first shape and an opposing second surface having a second shape, the shapes together providing a base optic power;

a central zone disposed about and intersecting an optical axis, the central zone including a first multifocal diffractive profile imposed on one of the shapes, the first multifocal diffractive profile having, for visible light, a primary diffraction order, a secondary diffraction order, and a diffractive add power corresponding to a difference in optical power between the secondary diffraction order and the primary diffraction order; and a plurality of peripheral zones disposed about the central zone comprising:

a first peripheral zone including a multifocal refractive profile imposed on one of the shapes having at least a first refractive power and a second refractive power;

a second peripheral zone including a second multifocal diffractive profile imposed on one of the shapes, the second multifocal diffractive profile having, for visible light, a primary diffraction order, a secondary diffraction order, and a diffractive add power corresponding to a difference in optical power between the secondary diffraction order and the primary diffraction order;

wherein the secondary diffraction order of the second diffractive profile has a diffraction efficiency at a visible light design wavelength that is greater than the secondary diffraction order of the first diffractive profile at the design wavelength;

wherein the diffraction efficiency at a visible light design wavelength of the secondary diffraction order of the first diffractive profile is between 15 percent and 25 percent and the remaining diffraction efficiency of the first diffractive profile goes to the primary diffraction order of the first diffractive profile; and wherein the diffraction efficiency at a visible light design wavelength of the secondary diffraction order of the second diffractive profile is between 25 percent and 35 percent and the remaining diffraction efficiency of the second diffractive profile goes to the primary diffraction order of the second diffractive profile.

29. The ophthalmic lens of claim 28, wherein the first peripheral zone is disposed about the central zone and second peripheral zone is disposed about the first peripheral zone.

30. The ophthalmic lens of claim 28, wherein the second peripheral zone is disposed about the central zone and first peripheral zone is disposed about the second peripheral zone.

31. The ophthalmic lens of claim 28, wherein the first refractive power and the second refractive power of the first peripheral zone differ by at least 1.5 Diopters.

32. The ophthalmic lens of claim 28, wherein the plurality of peripheral zones comprises a third peripheral zone disposed about the first and second peripheral zones, the third peripheral zone including a profile, the profile of the third peripheral zone being a diffractive profile or a multifocal refractive profile.

33. The ophthalmic lens of claim 28, wherein the plurality of peripheral zones comprise at least a third peripheral zone disposed about the first and second peripheral zones, the third peripheral zone having a constant refractive optical power and no diffractive optical power.

34. The ophthalmic lens of claim 28, wherein the multifocal diffractive profile of the central zone has a first optical characteristic, and the multifocal diffractive profile of the second peripheral zone has a second optical characteristic, and the first optical characteristic is different from the second optical characteristic.

35. The ophthalmic lens of claim 34, wherein the first optical characteristic is a first diffractive add power and the second optical characteristic is a second diffractive add power, the first and second diffractive add powers differing by at least 0.25 Diopters.

36. The ophthalmic lens of claim 34, wherein the first optical characteristic is a first step height of echelettes within the first peripheral zone and the second optical characteristic is a second step height of echelettes within the second peripheral zone, the first and second step heights being different.

37. The ophthalmic lens of claim 34, wherein the first optical characteristic is a first chromatic dispersion and the second optical characteristic is a second chromatic dispersion, the first and second chromatic dispersions being different.

38. The ophthalmic lens of claim 28, wherein at least one of the diffractive profiles comprises a plurality of echelettes, each of the echelettes having a different step height, the step heights decreasing with increasing radial distance from the optical axis.

* * * * *